United States Patent
Liu et al.

(10) Patent No.: US 9,283,189 B2
(45) Date of Patent: Mar. 15, 2016

(54) SUSTAINED-RELEASE PREPARATION OF IVABRADINE OR PHARMACEUTICALLY ACCEPTABLE SALTS THEREOF

(75) Inventors: Kai Liu, Jiangsu (CN); Yuxia Wu, Lianyungang (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 14/235,858

(22) PCT Filed: Jun. 18, 2012

(86) PCT No.: PCT/CN2012/077079
§ 371 (c)(1),
(2), (4) Date: Jan. 29, 2014

(87) PCT Pub. No.: WO2013/020416
PCT Pub. Date: Feb. 14, 2013

(65) Prior Publication Data
US 2014/0179683 A1 Jun. 26, 2014

(30) Foreign Application Priority Data
Aug. 5, 2011 (CN) .......................... 2011 1 0228902

(51) Int. Cl.
*A61K 9/20* (2006.01)
*A61K 31/55* (2006.01)
*B29C 43/00* (2006.01)

(52) U.S. Cl.
CPC ............. *A61K 9/2027* (2013.01); *A61K 9/2031* (2013.01); *A61K 31/55* (2013.01); *B29C 43/003* (2013.01)

(58) Field of Classification Search
None
See application file for complete search history.

(56) References Cited

U.S. PATENT DOCUMENTS

| 2002/0012701 A1* | 1/2002 | Kolter et al. .................. 424/468 |
| 2008/0200450 A1* | 8/2008 | Benatar et al. ........... 514/212.07 |

FOREIGN PATENT DOCUMENTS

| CN | 1482901 A | 3/2004 |
| CN | 101152155 A | 4/2008 |

OTHER PUBLICATIONS

Polyox (polyethylene oxide)—Applications in Pharma Industry, Sep. 22, 2010.*
Meeus, Direct compression versus granulation, Mar. 7, 2011.*
Shah et al. Evaluation of two new tablet lubricants, sodium stearyl fumerate and glyceryl behenate, Measurement of Physical parameters (compaction, ejection, and residual forces) in tableting process and the effects on dissolution rate, 1986.*
Wang, Wenping et al., "Formulation Optimization and Release Mechenism in Vitro of Matrix Tablets with Polyox-Mixture," Chinese Journal of Modern Applied Pharmacy, Oct. 2010, vol. 27, No. 1, pp. 35-38.

(Continued)

*Primary Examiner* — Robert A Wax
*Assistant Examiner* — Melissa Mercier
(74) *Attorney, Agent, or Firm* — Panitch Schwarze Belisario & Nadel LLP (57) ABSTRACT

Disclosed is a sustained-release preparation of ivabradine or pharmaceutically acceptable salts thereof. The preparation contains ivabradine or pharmaceutically acceptable salts thereof and a sustained-release framework material, wherein the sustained-release framework material is selected from polyoxyethylene, or a mixture of polyoxyethylene and polyvinyl acetate or polyvinyl pyrrolidone.

19 Claims, 3 Drawing Sheets

(56) References Cited

OTHER PUBLICATIONS

Nie, Shufang et al., "The Erosion Behavior of Matrix Tablets Using Polyethylene oxide matrices as Hydrophilic Polyme", Acta Pharmaceutica Sinica, 2005, vol. 40, No. 10, pp. 882-886.

Song, Weifeng et al, Study on compressed Hydrophilic Matrices Tablets of Polyox-WSR, Academic Journal of Guangdong College of Pharmacy, Dec. 2004, vol. 20, No. 6, pp. 599-601 and 609.

Int'l Search Report issued on Sep. 20, 2012, in Int'l Application No. PCT/CN2012/077079.

* cited by examiner

SUSTAINED-RELEASE PREPARATION OF IVABRADINE OR PHARMACEUTICALLY ACCEPTABLE SALTS THEREOF

CROSS-REFERENCE TO RELATED APPLICATIONS

This application is a Section 371 of International Application No. PCT/CN2012/077079, filed on Jun. 18, 2012, which was published in the Chinese language of Feb. 14, 2013, under International Publication No. WO 2013/020416 A1, and the disclosure of which in incorporated herein by reference.

FIELD OF THE INVENTION

The present invention relates to a sustained-release preparation of ivabradine or pharmaceutical acceptable salts thereof.

BACKGROUND OF THE INVENTION

Ivabradine is indicated for the symptomatic treatment of chronic stable angina pectoris in patients with normal sinus rhythm who have a contraindication or intolerance to beta-blockers.

Ivabradine, 7,8-dimethoxy-3-(3-[[(1S)(4,5-dimethoxy-benzocyclobutan-1-yl)methyl]-methylamino]propyl)-1,3,4,5-tetrahydro-2H-benzazepin-2-one, with a formula of $C_{27}H_{36}N_2O_5$, can be represented by the following general formula.

Ivabradine is the first pure heart rate-lowering agent and acts by selective inhibition of the cardiac pacemaker IF current that controls the spontaneous diastolic depolarization in the sinus node and regulates heart rate. Ivabradine's effects are selective to the sinus node and the new agent has no effect on intracardiac conduction, myocardial contractility or ventricular repolarization. Unlike beta-blockers, the most common current treatment for angina, ivabradine is free from sexual disturbances, respiratory side effects caused by constriction or spasm of the airways, bradycardia or rebound phenomena. Now that it is generally believed that heart rate-lowering is an important way of prevention and treatment of angina, this product has opened up a promising new way for the treatment of angina. It is one of the most significant advances in the past 20 years in the treatment of cardiovascular disease.

This invention provides an effective and significant, dose-dependent reduction in heart rate, which is also reflected in a reduction in the rate pressure product leading to a myocardial oxygen consumption. A large clinical program including almost 5000 patients has demonstrated the efficacy and tolerability of ivabradine. The antiangina and anti-ischemic efficacy of ivabradine was evaluated using a standardized exercise tolerance test in four double-blind randomized trials (two versus placebo, and one each versus the beta-blocker atenolol and the calcium channel blocker amlodipine) involving 3222 patients with chronic stable angina. Ivabradine (5 mg and 7.5 mg twice daily) was associated with a significant decrease in angina attacks, and the twice-daily dosage regimen provided uniform efficacy over 24 hours. A sustained reduction in heart rate was demonstrated in patients for at least one year (n=713) and no rebound effect occurred following the withdrawal of treatment. Moreover, no influence on glucose or lipid metabolism was observed.

At present, the rapid release preparations of ivabradine hydrochloride are for marketing. Ivabradine is rapidly and almost completely absorbed after oral administration with a peak plasma level reached in about 1 hour under fasting condition. Ivabradine is approximately 70% plasma protein bound and the volume of distribution at steady state is close to 100 L in patients. The maximum plasma concentration following chronic administration at the recommended dose of 5 mg twice daily is 22 ng/ml (CV=29%), and the average plasma concentration is 10 ng/ml (CV=38%) at steady state. Ivabradine is extensively metabolized by the liver and the gut by oxidation through cytochrome P450 3A4 (CYP3A4) only. The major active metabolite is an N-demethylated derivative. Ivabradine is eliminated with a main half-life of 2 hours (70~75% of the AUC) in plasma and an effective half-life of 11 hours. The total clearance is about 400 ml/min and the renal clearance is about 70 ml/min. Excretion of metabolites occurs to a similar extent via faeces and urine. About 4% of an oral dose is excreted unmetabolized in urine.

The kinetics of ivabradine is linear over an oral dose range of 0.5 mg~24 mg. The heart rate decreases almost linearly with increasing ivabradine and its main metabolite plasma concentration for doses of up to 15~20 mg twice daily. At high doses, the decrease in heart rate is no longer proportional to ivabradine plasma concentrations. When ivabradine is given in combination with strong CYP3A4 inhibitors, it may result in an excessive decrease in heart rate, although this risk reduced with moderate CYP3A4 inhibitors.

When the rapid release preparations of ivabradine hydrochloride are used clinically, the following phenomena may occur: the blood medicine concentration increases so fast that the heart rate decreases too fast (heart rate decreases persistently below 50 beats per minute), or the patient experiences symptoms related to bradycardia such as dizziness, fatigue or hypotension. When the plasma concentration is too high, there are side effects, while if it is too low, below the therapeutic concentration, there will be no therapeutic effects.

To reduce the peak-valley phenomenon of the blood medicine concentration of ivabradine, which causes a short increase of the blood medicine concentration and rapid elimination of ivabradine, a sustained release preparation of ivabradine or a pharmaceutically acceptable salt thereof is needed clinically.

At present, Chinese Patent No. CN1482901A, the patent related to ivabradine sustained release preparation, discloses a solid pharmaceutical composition of controlled release of ivabradine. This patent relates to a solid pharmaceutical composition which could be obtained by thermoforming, but no specific pharmaceutical preparation is provided. Moreover, hot extrusion forming technology and hot injection molding technology are used in this patent, which are too complex to be applied in industrialization. Besides, while using these two techniques, drugs and excipients have to be heated to 130° C., which will influence the stability of the drug.

The inventor has tried to use polymethacrylate Eudragit RL and RS to prepare sustained release skeleton tablets by the conventional methods of granulation compression, but a superior sustained release effect was not achieved. This indicates that the sustained release materials used in Chinese Patent No. CN1482901A and the techniques of hot extrusion forming and hot injection molding must be used together, otherwise, even if using Eudragit RL and RS as skeleton materials, a superior sustained release effect can not be achieved via conventional methods.

After researching a large amount of sustained release materials, it was discovered that using conventional sustained release materials, such as hydropropylmethyl cellulose, ethyl cellulose, sodium alginate, polymethacrylate, polyvinyl alcohol, and conventional preparation methods, such as granulation tableting or direct compression, cannot be used to prepare a sustained release preparation of ivabradine with a superior sustained release effect. However, the inventor has unexpectedly discovered that the polymers of polyoxyethylenes and polyvinyl acetates are appropriate for use as the sustained release skeleton materials of ivabradine or a pharmaceutically acceptable salt thereof, and that the sustained release preparation method of ivabradine or a pharmaceutically acceptable salt thereof can be made by conventional methods, such as granulation compression or direct compression. The product has better stability than the solid pharmaceutical composition in Chinese Patent No. CN 1482901A.

SUMMARY OF THE INVENTION

The object of the present invention is to provide a sustained-release preparation of ivabradine or a pharmaceutically acceptable salt thereof, which can moderate the peak-valley phenomenon of blood medicinal concentration and improve the drug therapeutic effect and safety, as well as reduce the frequency of administration and improve patient compliance.

The present invention provides a sustained-release preparation of ivabradine or pharmaceutically acceptable salts thereof comprising ivabradine or pharmaceutically acceptable salts thereof and one or more sustained-release skeleton materials, wherein the one or more sustained-release skeleton materials is selected from polyoxyethylene and polyvinyl acetate-polyvinylpyrrolidone polymer.

In a preferred embodiment, the sustained-release skeleton material used in the present invention is polyoxyethylene. The polyoxyethylene is a kind of Polyox water-soluble resin, which has a large molecular weight distribution of from 100,000 Da to 7,000,000 Da. The molecular weight of the Polyox water-soluble resin is preferably from 900,000 Da to 7,000,000 Da, more preferably from 1,000,000 Da to 7,000,000 Da, even more preferably from 4,000,000 Da to 7,000,000 Da, and most preferably from 5,000,000 Da to 7,000,000 Da.

In another preferred embodiment, the sustained-release preparation of the present invention uses polyvinyl acetate-polyvinylpyrrolidone polymer (Kollidon SR) as the sustained-release skeleton material.

In another preferred embodiment, a sustained-release preparation of the present invention uses the mixture of the two aforementioned polymers as the sustained-release skeleton material, that is it uses polyoxyethylene and polyvinyl acetate-polyvinylpyrrolidone polymer simultaneously. There is no limitation to the ratio of the two. The polyoxyethylene is a kind of Polyox water-soluble resin, the molecular weight of which is preferably from 900,000 Da to 7,000,000 Da, more preferably from 1,000,000 Da to 7,000,000 Da, even more preferably from 4,000,000 to 7,000,000 Da, most preferably from 5,000,000 Da to 7,000,000 Da.

The sustained-released preparation of the present invention contains 5 mg~20 mg ivabradine in each unit (based on the weight of ivabradine for the ivabradine pharmaceutically acceptable salts). The range of the proportion by weight of the skeleton materials in the sustained-release preparation can be very broad. Superior sustained-release preparations can be formulated as long as the proportion is more than 30%. Theoretically, the higher the proportion of the skeleton materials in the sustained-released preparation, the better the sustained-release effects are, but other pharmaceutical factors should be considered during the preparation. The preferred proportion is 30% to 95%, more preferably 50% to 95%, most preferably 50% to 90%.

As a preferred embodiment of the present invention, a sustained-release preparation of the present invention may also comprise other excipients such as diluents, adhesives, and lubricants, wherein the diluents may be pre-gelatinized starch, microcrystalline cellulose, calcium hydrogen phosphate or other pharmaceutically acceptable auxiliary; the adhesives may be polyvinylpyrrolidone, starch, carboxymethylcellulose, hydroxypropylmethyl cellulose or other pharmaceutically acceptable auxiliary; the lubricants may be magnesium stearate, glyceryl behenate, hydrogenated vegetable oil or other pharmaceutically acceptable auxiliary.

In a particular preferred embodiment, the sustained-release preparation of the present invention consists of ivabradine or pharmaceutically acceptable salts thereof, Polyox water-soluble resins, magnesium stearate and glyceryl behenate. In a further preferred embodiment, the molecular weight of the Polyox water-soluble resins is preferably from 900,000 Da to 7,000,000 Da, more preferably from 1,000,000 Da to 7,000,000, even more preferably from 4,000,000 Da to 7,000,000 Da, most preferably from 5,000,000 Da to 7,000,000 Da.

In another particular preferred embodiment, the present sustained-release preparation consists of ivabradine or pharmaceutically acceptable salts thereof, polyvinyl acetate-polyvinylpyrrolidone polymer, magnesium stearate, and glyceryl behenate; and optionally microcrystalline cellulose can be included.

In another particularly preferred embodiment, the present sustained-release preparation consists of ivabradine or pharmaceutically acceptable salts thereof, Polyox water-soluble resin, polyvinyl acetate-polyvinylpyrrolidone polymer, magnesium stearate and glyceryl behenate; and optionally calcium hydrogen phosphate can be included. In a further preferred embodiment, the molecular weight of the Polyox water soluble resin used is preferably from 900,000 Da to 7,000,000 Da, more preferably from 1,000,000 Da to 7,000,000 Da, even more preferably from 4,000,000 Da to 7,000,000 Da, most preferably from 5,000,000 Da to 7,000,000 Da.

The pharmaceutically acceptable salts of ivabradine can be in the form of the hydrochloride, hydrosulfate, sulfate, phosphate, citrate and the like.

The preferred dosage form of the present sustained-release preparation is tablets.

The present sustained-release preparation can be prepared by conventional techniques, such as granulation compression techniques or direct compression techniques, preferably direct compression techniques. A sustained-release preparation with superior sustained-release effects can be prepared by simple direct compression techniques, with using some excipients together, such as pre-gelatinized starch, microcrystalline cellulose, calcium hydrogen phosphate, glyceryl behenate, magnesium stearate and the like.

A particular preparation method comprises the following steps:
i. ivabradine or its pharmaceutically acceptable salt is pre-mixed with the sustained release skeleton materials after crushing;

ii. the mixture of ivabradine or its pharmaceutically acceptable salts and the sustained release skeleton materials obtained from Step 1 is mixed with the remainder of excipients;
iii. the mixture obtained from Step 2 is compressed and coated to give the matrix tablets.

The pharmaceutically acceptable salts of ivabradine can be in the form of hydrochloride, hydrosulfate, sulfate, phosphate, citrate and the like, preferably in the form of hydrochloride and hydrosulfate.

By researching the in vitro release rate and pharmacokinetics of the present sustained release preparation, and comparing to the pharmacokinetics of the normal rapid release preparation, the present invention has the following advantages:
i. effective drug blood concentration can be maintained for a longer time, the peak-valley phenomenon caused by frequent administration of the normal preparation can be avoided, and the safety, effectiveness and adaptability of the drug can be improved;
ii. the time the medicine is effective can be extended by a different releasing mechanism, the frequency of administration can be reduced, and the patient compliance can be improved;
iii. the product has good stability and the preparation technique is simple and has good reappearance, the industrialization degree is high, and large scale production can be achieved with conventional production equipment.

By performing the stability comparison experiments between the thermoforming mixture of ivabradine or its pharmaceutically acceptable salts and polymethacrylate disclosed by CN1482901A and the present sustained release preparation of ivabradine or pharmaceutically acceptable salts thereof, the results indicate that the present preparation has better stability.

DETAILED DESCRIPTION OF THE INVENTION

The present invention will be further illustrated by the following examples without any limitation of the present invention.

In the examples of the present invention, the addition amount of ivabradine pharmaceutically acceptable salts are all calculated by the ivabradine free base.

The chromatographic condition for the dissolution rate determination: C18 column and mobile phase is (0.01 mol/l $KH_2PO_4$ (adding 0.5% triethylamine, adjusted to pH 6.0 with phosphoric acid): methanol=80:20): methanol=60:40, the detection wavelength is 230 nm; the temperature of the column is 30° C., the flow rate is 0.65 ml/min.

The chromatographic condition for the related substances determination: C18 column and mobile phase A is 0.01 mol/l $KH_2PO_4$ (adding 0.5% triethylamine, adjusted to pH 6.0 with phosphoric acid): methanol=80:20, mobile phase B is methanol, the gradient elution is shown in the following table, the detection wavelength is 230 nm, the temperature of the column is 30° C., the flow rate is 0.75 ml/min.

The gradient elution condition

| t(min) | A (%) | B (%) |
|---|---|---|
| 0 | 90 | 10 |
| 10 | 70 | 30 |
| 15 | 55 | 45 |
| 35 | 55 | 45 |

Example 1

Comparative Example

The ivabradine hydrochoride extrudates were prepared according to the method of hot melt extrusion at 120° C. as in Chinese Patent No. CN1482901A.
Formula:

| Component | Formula 1 | Formula 2 |
|---|---|---|
| Ivabradine hydrochloride | 15 mg | 15 mg |
| Eudragit RLPO | 150 mg | 75 mg |
| Eudragit RSPO | — | 75 mg |

Figure 1:
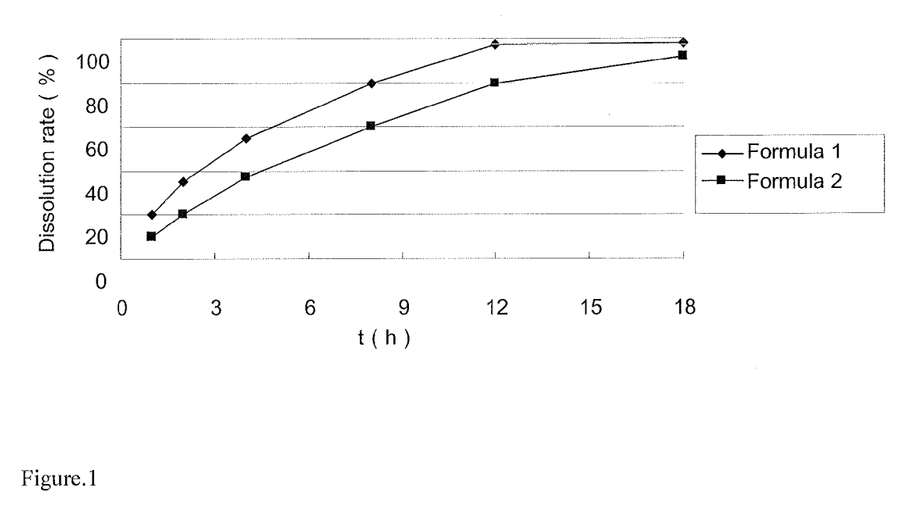
FIG. 1 shows the release profiles of the different formulas in Example 1.

The dissolution rate of the sustained release tablets in 900 ml water was determined by HPLC. The results are shown in Table 1. The release profiles are shown in FIG. 1.

TABLE 1

The dissolution rates of the different formulas in Example 1

| | Dissolution rate (%) | |
|---|---|---|
| t (h) | Formula 1 | Formula 2 |
| 1 | 20 | 10 |
| 2 | 35 | 20 |
| 4 | 55 | 37 |
| 8 | 80 | 60 |
| 12 | 97 | 80 |
| 18 | 98 | 92 |

Table 1 and FIG. 1 indicate that the ivabradine hydrochloride prepared by the method of Chinese Patent No. CN1482901A shows a superior sustained release effect, which can last 16 to 18 hours.

Example 2

Sustained release tablets were prepared respectively with hydropropylmethyl cellulose, ethyl cellulose, polymethacrylate (Eudragit RLPO, Eudragit RSPO), or polyvinyl alcohol as the skeleton material.

Formula:

| Component | Formula 3 | Formula 4 | Formula 5 | Formula 6 | Formula 7 | Formula 8 |
|---|---|---|---|---|---|---|
| Ivabradine hydrochloride | 15 mg | 15 mg | 15 mg | 15 mg | 15 mg | 15 mg |
| Hydroxypropylmethyl cellulose (K100M) | 150 mg | — | 120 mg | — | — | — |
| Ethyl cellulose (100 cp) | — | 150 mg | 50 mg | — | — | — |
| Eudragit RLPO | — | — | — | 150 mg | — | — |
| Eudragit RSPO | — | — | — | — | 150 mg | — |
| Polyvinyl acohol | — | — | — | — | — | 150 mg |
| Microcrystalline cellulose | 50 mg | 50 mg | 30 mg | 50 mg | 50 mg | 50 mg |
| Magnesium stearate | 2 mg | 2 mg | 2 mg | 2 mg | 2 mg | 2 mg |
| Hydroxypropylmethyl cellulose (E15) | q.s. | q.s. | q.s. | q.s. | q.s. | q.s. |

Preparation Method:

The crude materials were sifted through an 80-mesh sieve (pre-crushed if necessary). Each skeleton material was weighed according to the formula and mixed well. Then ivabradine hydrosulfate was added to the mixture and mixed well.

Hydroxypropylmethyl cellulose (E15) water solution was added to prepare soft materials and granulated through 20-mesh sieve. The granule was dried at 50° C. for 2 hours, and granulated by a 18-mesh sieve. Magnesium stearate was added at the same weight as the dry granule and mixed well. The mixture was compressed into tablets and coated.

Figure 2:
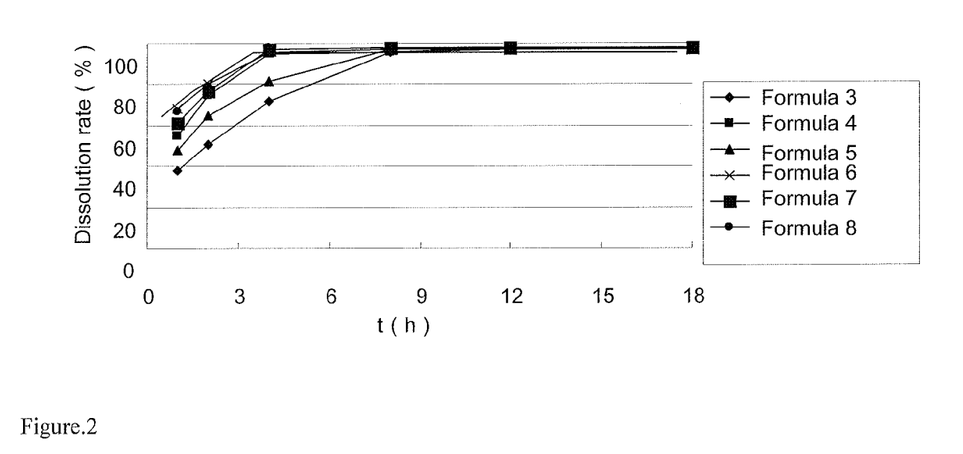
FIG. 2 shows the release profiles of the different formulas in Example 2.

The dissolution rate of the sustained release tablets in 900 ml water was determined by HPLC. The results are shown in Table 2. The release profiles are shown in FIG. 2.

TABLE 2

The results of the dissolution rates of different formulas in Example 2

Dissolution rate (%)

| t (h) | Formula 3 | Formula 4 | Formula 5 | Formula 6 | Formula 7 | Formula 8 |
|---|---|---|---|---|---|---|
| 1 | 38 | 55 | 48 | 68 | 61 | 67 |
| 2 | 51 | 75 | 65 | 80 | 77 | 79 |
| 4 | 72 | 95 | 82 | 96 | 97 | 98 |
| 8 | 96 | 96 | 97 | 97 | 98 | 98 |
| 12 | 98 | 97 | 98 | 97 | 98 | 98 |
| 18 | 98 | 98 | 98 | 97 | 98 | 98 |

From the research of the different formulas in Example 2, it is indicated that the sustained release tablets prepared with the conventional material or the sustained release materials disclosed in Chinese Patent No. CN1482901A and by the conventional techniques do not show good sustained release effect. When using hydroxypropylmethyl cellulose (K100M) as the skeleton material, it shows the most obvious sustained release effect, but it only can last for 8 hours.

Example 3

The sustained release tablets were prepared with polyoxyethylene (Polyox) as the skeleton materials.

Formula:

| Component | Formula 9 | Formula 10 | Formula 11 | Formula 12 | Formula 13 | Formula 14 | Formula 15 | Formula 16 |
|---|---|---|---|---|---|---|---|---|
| Ivabradine hydrochloride | 15 mg | 15 mg | 15 mg | 15 mg | — | — | — | — |
| Ivabradine hydrosulfate | — | — | — | — | 15 mg | 15 mg | 15 mg | 5 mg |
| Polyox N-750 (m.w. 300000 Da) | 150 mg | — | — | — | — | — | — | — |
| Polyox 205 (m.w. 600000 Da) | — | 150 mg | — | — | — | — | — | — |
| Polyox N-12K (m.w. 1000000 Da) | — | — | 150 mg | — | — | — | — | — |
| Polyox 303 (m.w. 7000000 Da) | — | — | — | 150 mg | 180 mg | 150 mg | 60 mg | 160 mg |
| Microcrystalline cellulose | 30 mg | 30 mg | 30 mg | — | — | 30 mg | 80 mg | 20 mg |
| Calcium hydrogen phosphate | — | — | — | 30 mg | — | — | 20 mg | — |
| Glyceryl behenate | 10 mg | 10 mg | 10 mg | 10 mg | 20 mg | 10 mg | 20 mg | — |
| Magnesium stearate | 2 mg | 2 mg | 2 mg | 2 mg | 2 mg | 2 mg | 2 mg | 2 mg |

Figure 3:
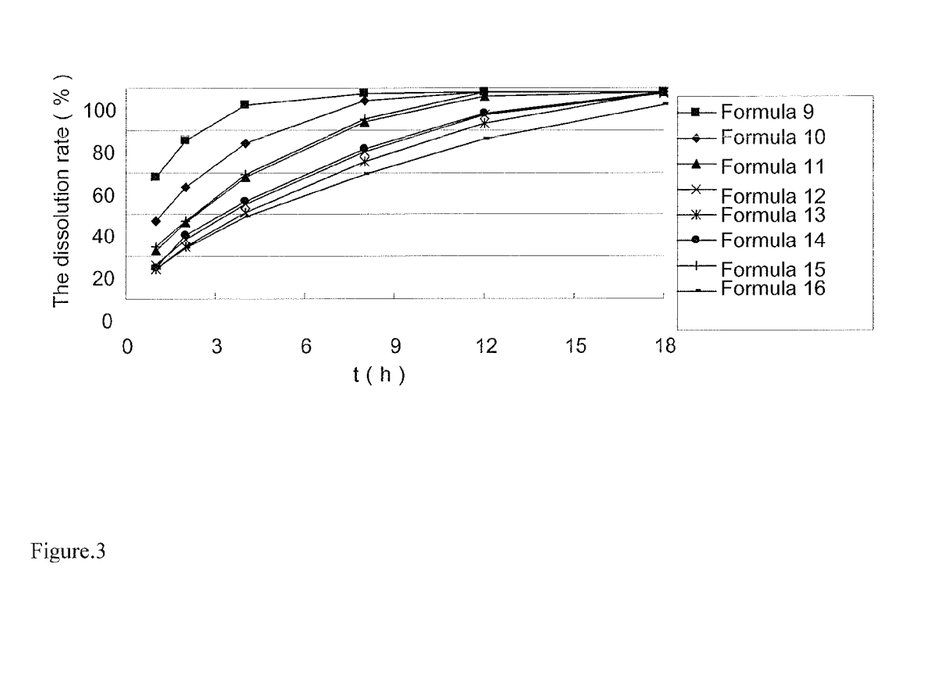
FIG. 3 shows the release profiles of the different formulas in Example 3.

Preparation Method:

The raw materials and the excipients were mixed well and pressed directly into sustained release tablets. The dissolution rate of the sustained release tablets in 900 ml water was determined by HPLC. The results are shown in Table 3. The release profiles are shown in FIG. 3.

TABLE 3

The results of the dissolution rates of different formulas in Example 3

Dissolution rate (%)

| t (h) | Formula 9 | Formula 10 | Formula 11 | Formula 12 | Formula 13 | Formula 14 | Formula 15 | Formula 16 |
|---|---|---|---|---|---|---|---|---|
| 1 | 58 | 37 | 23 | 16 | 14 | 15 | 25 | 14 |
| 2 | 75 | 53 | 36 | 28 | 25 | 30 | 37 | 24 |

TABLE 3-continued

The results of the dissolution rates of different formulas in Example 3

| t (h) | Dissolution rate (%) | | | | | | | |
|---|---|---|---|---|---|---|---|---|
| | Formula 9 | Formula 10 | Formula 11 | Formula 12 | Formula 13 | Formula 14 | Formula 15 | Formula 16 |
| 4 | 92 | 74 | 58 | 45 | 41 | 46 | 59 | 39 |
| 8 | 97 | 94 | 84 | 70 | 65 | 71 | 85 | 59 |
| 12 | 98 | 98 | 96 | 87 | 83 | 88 | 98 | 76 |
| 18 | 98 | 98 | 98 | 97 | 98 | 98 | 98 | 92 |

Table 3 and FIG. 3 indicate that superior sustained release effects were obtained when the sustained release tablets were prepared with polyoxyethylene of high molecular weight (Polyox, the molecular weight is greater than 1,000,000 Da) by direct compression. The sustained release tablets prepared with polyoxyethylene of low molecular weight (formulas 9 and 10) release too fast to meet the required sustained release effect. Moreover, it also proves that the higher the proportion of the skeleton material and the active component, the better the sustained released effect is (formula 13 and 16).

Example 4

The sustained release tablets were prepared with the skeleton material mixture composed of polyoxyethylene, a mixture of polyvinyl acetate and polyvinylpyrrolidone (PVP). Formula:

| Component | Formula 17 | Formula 18 | Formula 19 | Formula 20 |
|---|---|---|---|---|
| Ivabradine hydrochloride | 15 mg | 15 mg | — | — |
| Ivabradien hydrosulfate | — | — | 15 mg | 15 mg |
| Polyox 303 (m.w. 7000000 Da) | — | 50 mg | — | — |
| The mixture of polyvinyl acetate and PVP (Kollidon SR) | 150 mg | 100 mg | 180 mg | — |
| The water dispersion of polyvinyl acetate (Kollicoat SR 30D) | — | — | — | 500 mg |
| Microcrystalline cellulose | 30 mg | — | — | 50 mg |
| Calcium hydrogen phosphate | — | 30 mg | — | — |
| Glyceyl behenate | 10 mg | 10 mg | 20 mg | 10 mg |
| Magnesium stearate | 2 mg | 2 mg | 2 mg | 2 mg |

Figure 4:
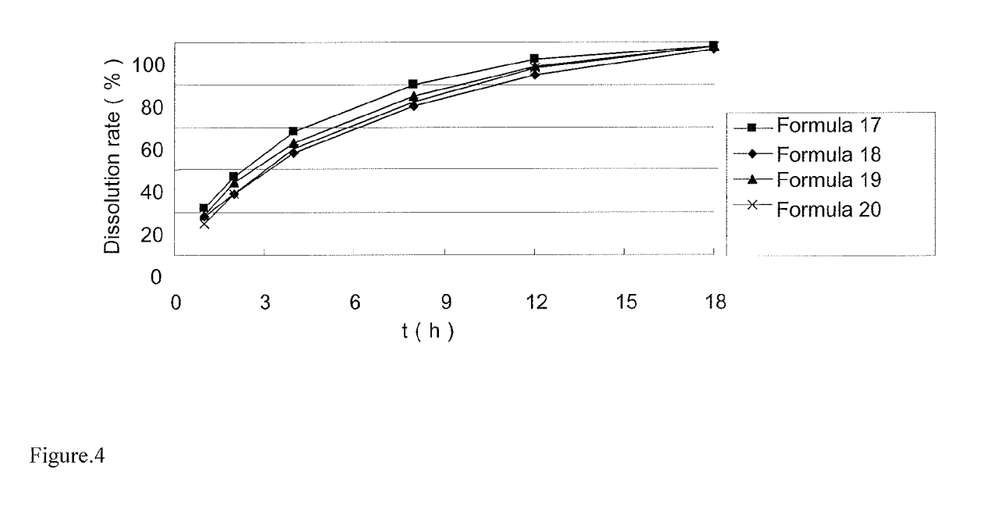
FIG. 4 shows the release profiles of the different formulas in Example 4.

The Preparation Method:

The sustained release tablets of formulas 17, 18, and 19 were prepared by direct compression. The sustained release tablets of formula 20 were prepared by fluidized bed granulation compression. The dissolution rate of the sustained release tablets in 900 ml water was determined by HPLC. The results are shown in Table 4. The release profiles are shown in FIG. 4.

TABLE 4

The results of the dissolution rates of different formulas in Example 4

| t (h) | Dissolution rate (%) | | | |
|---|---|---|---|---|
| | Formula17 | Formula18 | Formula19 | Formula20 |
| 1 | 22 | 18 | 19 | 15 |
| 2 | 37 | 29 | 34 | 29 |
| 4 | 58 | 48 | 53 | 50 |
| 8 | 80 | 70 | 75 | 72 |
| 12 | 92 | 85 | 89 | 88 |
| 18 | 98 | 97 | 98 | 98 |

From Table 4 and FIG. 4 it is indicated that superior sustained release effects are achieved when using the combination of polyoxyethylene, polyvinyl acetate and polyvinylpyrrolidone (PVP) mixture as the skeleton materials (formula 18).

Example 5

Stability Experiment

The products from formulas 1, 2, 3, and 19 were packaged with aluminum foil bags and stability tests were carried out in the condition of 40° C./RH75% and 30° C./RH65%. The results are shown in Table 5.

TABLE 5

The results of the stability comparison experiments

| Experimental conditions | t | Related substance (%) | | | |
|---|---|---|---|---|---|
| | | Formula 1 | Formula 2 | Formula 13 | Formula 19 |
| | Initial | 0.67 | 0.87 | 0.14 | 0.15 |
| 30° C. RH65% | 1 month | 0.95 | 1.12 | 0.15 | 0.15 |
| | 3 month | 1.06 | 1.35 | 0.17 | 0.18 |
| | 6 month | 1.23 | 1.56 | 0.17 | 0.18 |
| 40° C. RH75% | 1 month | 1.08 | 1.23 | 0.17 | 0.18 |
| | 3 month | 2.08 | 2.37 | 0.19 | 0.20 |
| | 6 month | 4.05 | 4.53 | 0.77 | 0.73 |

From the results, it is indicated that the related substances increases obviously in the stability experiments of the composition prepared by the existing technology, and that the present sustained-release preparation shows better stability than the composition prepared by the existing technology.

Example 6

Pharmacokinetic Studies

Figure 5:
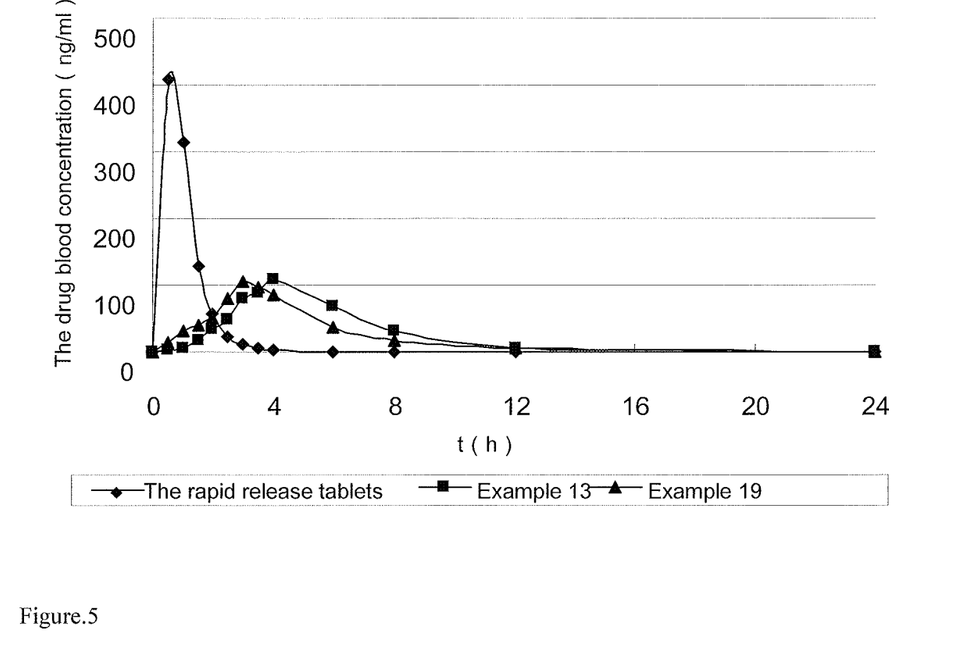
FIG. 5 shows the pharmacokinetic profiles of Beagle dog in prescription 13, prescription 19 and ivabradine hydrochloride rapid release tablets (15 mg).

The pharmacokinetic comparison experiment of Beagle dog was performed for the preparation of formulas 13, 19 and the ivabradine hydrochloride rapid release tablets (15 mg) (7.5 mg, 2 pieces, Servier, France). The results are shown in FIG. 5.

Comparing the pharmacokinetic results in Beagle dogs of the present sustained release preparation and the rapid release preparation, the $C_{max}$ of the present preparation is obviously lower than that of the rapid release preparation, and the present preparation overcomes the side effects of the rapid decreasing of heart rate caused by the rapid increasing of $C_{max}$ after administration. Furthermore, the present sustained-release preparation prolongs the in vivo drug retention time up to 12 hours, which exhibits superior sustained release effects.

Due to the detailed description of the particular embodiments of the present invention, some modifications and variants are obvious for the person skilled in the art and are included in the scope of the present invention.

What is claimed is:

1. A sustained release preparation of ivabradine or a pharmaceutically acceptable salt thereof, comprising ivabradine or the pharmaceutically acceptable salt thereof and sustained release skeleton materials, wherein the sustained release skeleton materials are one or more selected from the group consisting of polyoxyethylene and a mixture of polyvinyl acetate and polyvinylpyrrolidone, such that the sustained release preparation prolongs in vivo retention time of ivabradine for up to at least about twelve hours, and wherein the sustained release preparation is prepared by a process comprising a direct compression tabletting process or granulation tabletting process.

2. The sustained release preparation according to claim 1, wherein the molecular weight of polyoxyethylene is 900,000 Da to 7,000,000 Da.

3. The sustained release preparation according to claim 1, comprising 30% to 95% of the sustained release skeleton materials by weight.

4. The sustained release preparation according to claim 1, comprising 5 mg to 50 mg ivabradine or the pharmaceutically acceptable salt thereof calculated by the weight of ivabradine per unit dosage form.

5. The sustained release preparation according to claim 1, comprising a pharmaceutically acceptable excipient.

6. The sustained release preparation according to claim 5, wherein the excipient comprises one selected from the group consisting of diluents, adhesives, lubricants, and a combination thereof.

7. The sustained release preparation according to claim 6, wherein the diluents are one or more selected from the group consisting of pre-gelatinized starch, microcrystalline cellulose, and calcium hydrogen phosphate.

8. The sustained release preparation according to claim 6, wherein the adhesives are one or more selected from the group consisting of polyvinylpyrrolidone, starch, carboxymethyl cellulose, and hydroxypropylmethyl cellulose.

9. The sustained release preparation according to claim 6, wherein the lubricants are one or more selected from the group consisting of magnesium stearate, glyceryl behenate, and hydrogenated vegetable oil.

10. The sustained release preparation according to claim 5, wherein the sustained release preparation comprises ivabradine or the pharmaceutically acceptable salt thereof, polyoxyethylene, magnesium stearate, and glyceryl behenate.

11. The sustained release preparation according to claim 5, wherein the sustained release preparation comprises ivabradine or the pharmaceutically acceptable salt thereof, polyoxyethylene, a mixture of polyvinyl acetate and polyvinylpyrrolidone, magnesium stearate and glyceryl behenate.

12. The sustained release preparation according to claim 1, wherein the ivabradine pharmaceutically acceptable salt is one or more selected from the group consisting of hydrochloride salt, hydrosulfate, sulfate, phosphate and citrate.

13. The sustained release preparation according to claim 1, wherein the sustained release preparation is a tablet.

14. A method of preparing the sustained release preparation according to claim 13, wherein the method comprises a direct compression tabletting process or granulation compression tabletting process.

15. The preparation method according to claim 14, wherein the granulation tabletting compression process comprises fluidized bed granulation compression.

16. The sustained release preparation according to claim 1, wherein the molecular weight of polyoxyethylene is 5,000,000 Da to 7,000,000 Da.

17. The sustained release preparation according to claim 3, comprising 50% to 90% of the sustained release skeleton materials by weight.

18. The sustained release preparation according to claim 1, comprising 5 mg to 20 mg ivabradine or the pharmaceutically acceptable salt thereof calculated by the weight of ivabradine per unit dosage form, polyoxyethylene having a molecular weight of 5,000,000 Da to 7,000,000 Da, a mixture of polyvinyl acetate and polyvinylpyrrolidone, magnesium stearate and glyceryl behenate.

19. The method of preparing the sustained release preparation according to claim 14, comprising a direct compression tabletting process.

* * * * *